United States Patent [19]
Coussens et al.

[11] Patent Number: 5,874,303
[45] Date of Patent: *Feb. 23, 1999

[54] SUSTAINABLE CELL LINE FOR THE PRODUCTION OF MAREK'S DISEASE VACCINES

SUSTAINABLE CELL LINE FOR THE PRODUCTION OF MAREK'S DISEASE VACCINES

CROSS-REFERENCE TO RELATED APPLICATION

This is a divisional of application Ser. No. 08/670,272 filed on Jun. 21, 1996, which is a continuation in part of U.S. application Ser. No. 08/549,045, filed Oct. 27, 1995, entitled "Sustainable Cell Line Infected With Marek's Disease Virus" by inventors Amin Abujoub and Paul M. Coussens.

BACKGROUND OF THE INVENTION (1) Summary of the Invention

The present invention relates to a sustainable chicken cell line infected with vaccine strains of Marek's disease virus (MDV). In particular, the present invention relates to cell lines infected with vaccine strains of turkey herpesvirus (HVT) and vaccine strains of serotype-2 MDV which can be used as live virus vaccine to protect poultry against Marek's disease, wherein the MDV resides in these cultures as a lytic or non-lytic infection, depending upon growing conditions.

(2) Background of the Invention

Marek's Disease

Marek's disease (MD), is the most common clinical neoplastic condition of any animal, including humans, on earth (H. G. Purchase, in "Marek's Diseases: Scientific Basis and Methods of Control: Clinical disease and its economic impact." (L. N. Payne, Ed.), Martinus Nijoff Publishing, Boston, Mass., pp. 17–42. (1985)). MDV is a highly contagious lymphoproliferative herpesvirus. There are three MDV serotypes: the oncogenic serotype-1 (MDV-1) ; the nononcogenic serotype-2 (MDV-2) ; and the non-oncogenic serotype-3, turkey herpesvirus (HVT) (B. W. Calnek and R. L. Witter, in "Diseases of Poultry: Marek's Disease" (B. W. Calnek et al., Eds.), Iowa State University Press, Ames, Iowa pp. 342–385, (1991)).

Replication of MDV and HVT is typical of other cell-associated herpesviruses and has been extensively reviewed (L. J. N. Ross, in "Marek's Diseases: Scientific Basis and Methods of Control: Molecular Biology of the Virus." (L. N. Payne, Ed.), Martinus Nijoff Publishing, Boston, Mass., pp. 113–150 (1985)). The three general types of cell-virus interactions recognized are: productive infection, latent, and transforming. The sequence of events in MDV-1 infected birds leading to transformation include, 1) initial lytic growth in B-cells, 2) a latent phase involving infected T-cells, 3) a second round of lytic infection, coincident with permanent immunosuppression, and 4) oncogenic transformation (B. W. Calnek and R. L. Witter, in "Diseases of Poultry: Marek's Disease" (B. W. Calnek et al., Eds.), Iowa State University Press, Ames, Iowa, pp. 342–385 (1991)). The sequence of events in MDV-2 and HVT infected birds appears to be limited to an initial lytic phase followed by latency in non T-cells or latency without oncogenic transformation (B. W. Calnek and R. L. Witter, in "Diseases of Poultry: Marek's Disease" (B. W. Calnek et al., Eds.), Iowa State university Press, Ames, Iowa, pp. 342–385 (1991)).

Avian Cell Lines

The poultry industry has always recognized the need for continuous avian cell lines that could be used for producing Marek's disease vaccines and simplify development of recombinant MDV vectors for polyvalent vaccines. Although many avian cell lines have been developed (K. Nazerian, Avian Pathol. 16:527–544 (1987)), until the present invention, no cell line could substitute for chicken embryo fibroblast (CEF) cells in vaccine production. Previous cell lines failed because they were either derived from virally transformed cells or, if derived from chemically transformed cells, the cells produced tumors when inoculated into chickens, or the maximum titer of virus recoverable from the cell line was insufficient for commercial production. Therefore, poultry vaccine producers continue to use primary CEF cells for producing Marek's disease and other live and killed vaccines, an expensive and labor intensive process dependent on a continual source of specified pathogen free (SPF) eggs for preparing CEF.

Marek's Disease Vaccines

Marek's disease vaccines are the most widely used vaccines in the poultry industry. Since development of live virus Marek's disease vaccines in the late 1970's, losses to Marek's disease have been significantly reduced (B. W. Calnek and R. L. Witter, in "Diseases of Poultry: Marek's Disease" (B. W. Calnek et al., Eds.), Iowa State University Press, Ames, Iowa, pp. 342–385 (1991)). The most widely used Marek's disease vaccines are live HVT or a bivalent mixture of live HVT and the pathogenic serotype 2 MDV. The bivalent mixture of HVT and serotype 2 MDV synergistically affords greater protection against Marek's disease especially in those situations where HVT is not fully effective (R. L. Witter, Avian Pathol. 11:49–62 (1982); R. L. Witter and L. F. Lee, Avian pathol. 13:75–92 (1984); R. L. Witter, "Marek's Diseases:Scientific Basis and Methods of Control: Principles of Vaccination." (L. N. Payne, Ed.), Martinus Nijoff Publishing, Boston, Mass. pp. 203–250 (1985)).

Marek's disease vaccines have achieved worldwide use (M. Pattison, "Marek's Diseases: Scientific Basis and Methods of Control: Control of Marek's disease by the poultry industry: practical considerations." (L. N. Payne, Ed.), Martinus Nijoff Publishing, Boston, Mass., pp. 341–350 (1985)), even though production of these vaccines requires weekly preparation of CEF cells. Therefore, vaccine production is very dependent on a continuous and reliable supply of fertile eggs from specified pathogen free (SPF) flocks. SPF flocks are raised under special conditions and are regularly demonstrated to be free of avian pathogens (D. H. Thornton, "Marek's Diseases: Scientific Basis and Methods of Control: quality control and standardization of vaccines." (L. N. Payne, Ed.), Martinus Nijoff Publishing, Boston, Mass., pp. 267–292 (1985)). Any disruption in the supply of fertile SPF eggs would disrupt production of MDV vaccines. A continuous cell line for MDV vaccine production would have great economic benefits for the worldwide poultry industry.

Current Marek's disease vaccines are either suspensions of infected CEF or cell-free virus suspensions made from sonicated CEF infected with vaccine strains of Marek's disease virus. Since there are no sustainable cell lines suitable for propagating MDV, the MDV vaccine industry uses primary CEF for production of vaccine virus (A. E. Churchill, "Marek's Diseases: Scientific Basis and Methods of Control: Production of vaccines." (L. N. Payne, Ed.), Martinus Nijoff Publishing, Boston, Mass., pp. 251–266 (1985)). Primary CEFs have a finite life span (approximately two to three weeks) and must be prepared every one or two weeks, increasing costs for producing MDV vaccines.

The number of passages in CEF cell culture is limited for MDV. Continual cultivation of all three MDV serotypes in CEF results in attenuation of serotype-1 MDV and for serotype-2 and 3, loss of protective efficacy against MDV. The attenuation of serotype-1 MDV in culture has been extensively investigated and has been correlated to an expansion in the het region of the viral genome. This expansion can be easily monitored by Southern analysis or by PCR. The reason for loss of protective efficacy for high passage serotype-2 and -3 MDV is not known.

H. Ogura and T. Fujiwara (Acta Med. Okayama 41:141–143 (1987)) established a cell line (CHCC-OU2) by chemically transforming chicken embryo cells. The cell line was fibroblastic in appearance, contact inhibited, and did not form colonies in agar. The authors showed that CHCC-OU2 cell lines were not malignantly transformed, did not produce endogenous avian retroviruses, but were capable of supporting replication of Newcastle disease virus and several subgroups of avian retroviruses. However, the authors did not extend their study to the replication of other avian viruses such as Marek's disease virus and infectious bursal disease virus.

OBJECTS

It is therefore an object of the present invention to provide a sustainable cell line for production of MDV vaccines. Further still, it is the object of the present invention to provide a method for producing the sustainable MDV vaccine cell lines. Further still, it is an object of the present invention to provide a method for producing the MDV vaccine cell lines which is economical and a method for using the vaccine cell lines which is effective. Further still, it is an object of the present invention to provide a method for infecting an avian with the MDV vaccine cell lines to provide immunity against Marek's disease. These and other objects will become increasingly apparent by reference to the following description and drawings.

DESCRIPTION OF PREFERRED EMBODIMENTS

The present invention relates to a sustainable Marek's disease virus infected chicken cell line in a monolayer culture derived from chick embryo cells (CEC) which are chicken helper factor (Chf) negative and virus-free and which have been treated with a chemical mutagen and then are infected with MDV, which cell line is able to infect avians in vivo, wherein the MDV can be maintained as a non-lytic or lytic infection in the cell line.

Further, the present invention relates to a method for producing a sustainable latent Marek's disease virus infected chicken cell line in a non-confluent monolayer culture which comprises: combining chick embryo cells, which are chicken helper factor negative and virus-free and have been treated with a chemical mutagen, with MDV in a culture medium so that the CEC are infected with MDV; and purifying the MDV infected CEC from uninfected CEC; and propagating the MDV infected CEC to produce the cell line in a monolayer culture, wherein the MDV can be maintained as a non-lytic or lytic infection in the cell line.

The present invention relates to a method for infecting an avian with Marek's disease virus which comprises: providing a vaccine produced by a sustainable Marek's disease virus infected chicken cell line maintained as monolayer culture derived from chick embryo cells which are chicken helper factor negative and virus-free and which have been treated with a chemical mutagen and then are infected with MDV, wherein the MDV can be maintained as a non-lytic or lytic infection in the cell line, which cell line is able to infect avians in vivo; and inoculating the avian with the vaccine.

The present invention relates to an avian vaccine in dosage unit form containing a sustainable Marek's disease virus infected fibroblast cell line derived from chick embryo cells which are chicken helper factor negative and virus-free and which have been treated with a mutagenic agent and then are infected with MDV maintained over time as a monolayer wherein the MDV can be maintained as a non-lytic or lytic infection in the cell line.

MDV is used to describe any of the three MDV serotypes, i.e. serotype 1, serotype 2, or serotype 3 also known as HVT, and MDV-OCL can refer to any cell line comprising any of the three MDV serotypes either singly or in combination. MDV or MDV-OCL is the subject of the present invention and are used herein except in cases where specific embodiments, cell lines comprised of specific MDV strains, are provided as examples. Cell lines infected with specific strains of MDV are identified as follows: MDV-OU2 or MDV-OU2.2 or MDV-OU2.1 refer to any cell line comprising serotype 1 MDV strain MD11. SB1-OCL refers specifically to any cell line comprising serotype 2 MDV strain SB1. FC126-OCL refers specifically to any cell line comprising serotype 3 MDV strain FC126.

Experiments described in U.S. patent application Ser. No. 08/549,045 filed Oct. 27, 1995, entitled, "Sustainable Cell Line infected with Marek's Disease Virus", demonstrated that CHCC-OU2 cell lines can be infected with serotype-1 MDV. MDV was stably maintained in the cell lines and the infected cells grew continuously. However, the manner of infection was unexpected. Unlike MDV infection of CEF, or other avian cells, plaque formation on infected CHCC-OU2 monolayers was not visible and infectious virus was not produced until the monolayer became confluent and the cell lines had become contact-inhibited. Upon contact inhibition, cytopathic effect (CPE) from MDV infection became evident and infectious virus was produced. Prior to contact inhibition, MDV is maintained in the CHCC-OU2 cell lines in a latent or semi-latent state. On the other hand CEF, or other avian cells, infected with MDV develop plaques and produce infectious virus regardless of whether the cell monolayer is confluent or sub-confluent. Therefore, infection of CHCC-OU2 cells plated in culture dishes at a density comparable to the typical density used for CEF would not develop plaques and infectious virus for two weeks or more whereas in the case of infected CEF, plaques develop two to three days post-infection. This is because the CHCC-OU2 cell lines have a doubling time of approximately three to five days compared to CEF which has a doubling time of 24 hours.

Western blots of proteins isolated from sub-confluent MDV infected CHCC-OU2 cell lines (MDV-OU2 cell lines) detected expression of MDV proteins typically expressed during latency, pp38 and pp14, but not late proteins such as gB, gC, gE, and gI, all proteins expressed during productive infection (U.S. patent application Ser. No. 08/549,045, filed Oct. 27, 1995 entitled, "Sustainable Cell Line Infected with marek's Disease Virus"). Immunofluorescent assays of sub-confluent MDV-OU2 cell lines also could only detect pp38 and pp14. Late proteins such as gB could only be detected in immunofluorescent assays of confluent cell lines. These results indicated that MDV exists in sub-confluent MDV-OU2 cell lines as a latent infection.

MDV-OU2 cell lines transferred MDV infection to primary CEF and induced clinical signs of Marek's disease in susceptible chickens inoculated with MDV-OU2 cell lines (U.S. patent application Ser. No. 08/549,045, filed Oct. 27, 1995). Peripheral blood lymphocytes collected from infected birds at various times post-inoculation produced MDV plaques when cultivated on CEF monolayers. DNA isolated from infected bird kidneys also demonstrated MDV infection by PCR. Finally, histological evaluation revealed lymphocytic infiltration and early, active lymphomas in various tissues isolated from inoculated birds. These results clearly demonstrate that MDV-OU2 cell lines can transfer MDV to primary cells and to chickens.

The present invention shows that: 1) MDV cell lines contain MDV in a latent-like state, 2) infectious MDV can be recovered from MDV cell lines by allowing the cells to grow to confluence, 3) the MDV cell lines can be sustained indefinitely, and 4) MDV is stably maintained in the MDV cell lines.

It was unexpected that MDV was maintained in a latent or latent-like state in sub-confluent CHCC-OU2 cell lines and that MDV induced CPE does not become evident until after the cells reach a confluent level. CHCC-OU2 cell lines harboring MDV in a latent-like state are able to divide and transfer MDV to daughter cells. As long as MDV infected CHCC-OU2 cell lines are passaged at sub-confluent levels in culture, pure MDV-OCL cell lines can be established. CPE and infectious virus can be produced by allowing the MDV-OCL cell lines to reach confluence. However, sub-confluent MDV-OCL cell lines can still transfer virus to CEF and induce immunity when in a vaccine.

Serotype 3 MDV (HVT strain FC126-OCL) infected CHCC-OU2 cell lines were deposited under the terms of the Budapest Treaty at the American Type Culture Collection (ATCC), 10801 University Blvd., Manassas, Va. 20110-2209 U.S.A., on Feb. 22, 1996 under accession number CRL-12052 and is available upon request by name and number. CRL-12052 is irrevocably available from the ATCC for the life of the patent. Similarly, serotype 2 MDV (strain SB1-OCL) infected CHCC-OU2 cell lines were deposited under the terms of the Budapest Treaty at the ATCC on Feb. 22, 1996 as accession number CRL-12053 and is available upon request by name and number. CRL-12053 is irrevocably available from the ATCC for the life of the patent. Serotype 1 was deposited under the terms of the Budapest Treaty at the ATCC on Sep. 28, 1995 under accession number CRL-11985 (MDV OU2.2). CRL-11985 will be irrevocably available from the ATCC for the life of the patent. No permission or license is granted other than as required by the deposits.

Distinguishing Characteristics of CHCC-OU2, SB1-OCL, MDV-OCL and FC126-OCL Cell Lines CHCC-OU2 cell lines are cells capable of continuous growth in cell culture and were derived from chicken embryo cells transformed by treatment with methylnitronitrosoguanidine (MNNNG). CHCC-OU2 cells exhibit a fibroblastic appearance and display anchorage dependent growth. The CHCC-OU2 cell line was deposited under the terms of the Budapest Treaty at the ATCC under accession number CRL-12302. The CHCC-OU2 cell line is irrevocably available from the ATCC for the life of the patent.

The CHCC-OU2 cell line that is the subject of the present invention can be distinguished from other avian cell lines by the following criteria. CHCC-OU2 cells of the present invention have a doubling time of 3 to 5 days dependent on the initial cell density. Cells plated in culture at low cell densities (not more than $3.3 \times 10^4$ cells/cm$^2$) replicate at an initial rate that is less than cells plated at cell densities within the range of $3.3 \times 10^4$ to $5.6 \times 10^4$ cells/cm$^2$. Furthermore, replication of CHCC-OU2 cells is contact-inhibited and CHCC-OU2 cells do not form colonies in soft agar. This characteristic is unique to the CHCC-OU2 cells of the present invention as other avian cell lines do not display a contact-inhibition phenotype, and many transformed cell lines derived by treatment with MNNNG form colonies in soft agar. Once the CHCC-OU2 monolayer reaches an average cell density of $1.7 \times 10^5$ cells/cm$^2$ the cells enter a $G_o$ phase and cease to replicate. CHCC-OU2 cells unlike all other avian cell lines are non-malignant and do not form tumors when injected into birds.

Further distinguishing characteristics of CHCC-OU2 cells of the present invention comprise the following.

1) CHCC-OU2 cell line expresses major histocompatibility complex class 1 (MHC class 1) molecules. The CHCC-OU2 cells exhibit an MHC class I $B^{13}$ haplotype and have strong cross-reactivity to antisera against the MHC class 1 $B^5$ haplotype. Chicken embryo fibroblasts express little detectable MHC class 1 molecules. No other avian cell line or transplantable tumor appears to have an MHC class 1 $B^{13}/B^5$ genotype (Nazerian Avian path. 16:527–544) (1987)).

2) CHCC-OU2 cells contain sequences from endogenous avian retroviruses ev1, ev6, ev15 as evidenced by Southern transfers of BamHI, HindIII or SacI digested CHCC-OU2 DNA hybridized to avian retrovirus probe RAV-2. Over twenty endogenous avian retrovirus subtypes exist. Since the subtypes are inherited by Mendelian genetics, the specific combination of ev within a cell line or bird can serve as a marker for cell lines or birds. The endogenous retrovirus phenotype of CHCC-OU2 cells is group specific antigen negative (ga$^-$) and chick helper factor negative (chf$^-$). While CHCC-OU2 cells contain ev sequences integrated into the genome, the cells do not produce infectious retroviruses as evidenced by lack of reverse transcriptase activity and absence of virus particles by electron microscopy.

Figure 3:
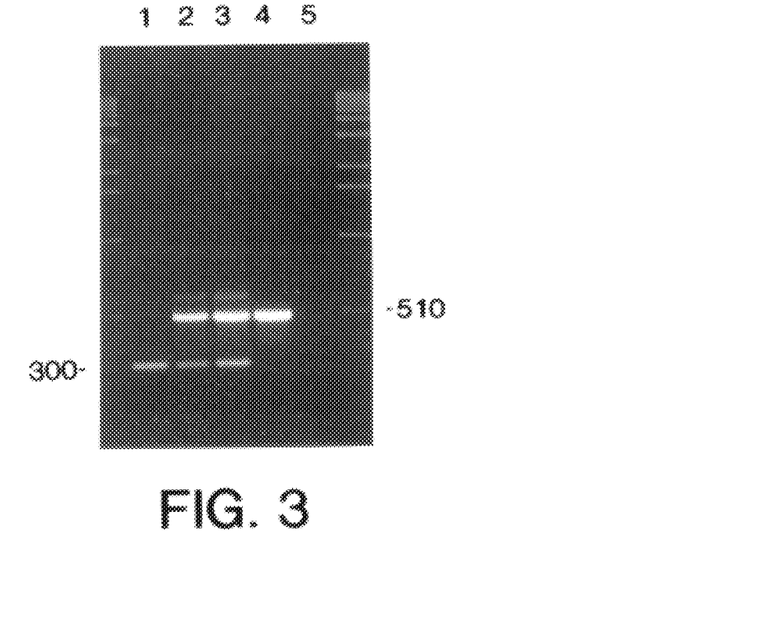
FIG. 3 is a photograph of an agarose gel showing a PCR amplification assay of CHCC-OU2 DNA for ev1. DNA from CHCC-OU2, avian cells heterozygous for ev1, or lacking ev1 were used for PCR amplification. The PCR products were electrophoresed on a 1% agarose gel, stained with ethidium bromide and the PCR products visualized under ultraviolet light. CHCC-OU2 DNA PCR products are in lane 1, PCR products from DNA template containing ev1 are in lane 2, PCR products from DNA template containing ev1 and ev6 are in lane 3, and PCR products from DNA template containing ev15 but not ev1 are in lane 4. Lane 5 is a control containing the ev1 primer set and no DNA template. Flanking one kb ladder marker (GIBCO BRL, Life Technologies, Gaithersburg, Md.) were used for size determination of the PCR products.
Figure 4:
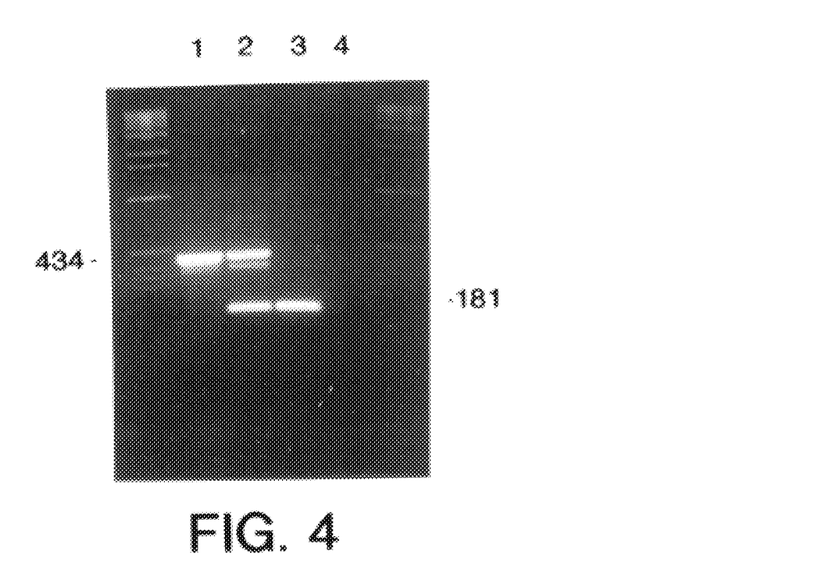
FIG. 4 is a photograph of an agarose gel showing a PCR amplification assay of CHCC-OU2 DNA for ev15. DNA from CHCC-OU2, avian cells heterozygous for ev15, or lacking ev15 were used for PCR amplification. The PCR products were electrophoresed on a 1% agarose gel, stained with ethidium bromide and the PCR products visualized under ultraviolet light. CHCC-OU2 DNA PCR products are in lane 1, PCR products from DNA template containing ev15 are in lane 2, and PCR products from DNA template containing ev1 but not ev15 are in lane 3. Lane 4 is a control containing the ev15 primer set and no DNA template. Flanking one kb ladder marker (GIBCO BRL, Life Technologies, Gaithersburg, Md.) were used for size determination of the PCR products.

Birds may be homozygous, heterozygous or completely lack any specific ev subtype. PCR amplification assays have been developed to determine whether a bird is homozygous or heterozygous for ev1 or ev15. PCR amplification of DNA from CHCC-OU2 cells revealed that the cells are homozygous for both ev1 (FIG. 3) and ev15 (FIG. 4). A PCR assay for ev6 is not yet available.

3) CHCC-OU2 cells are susceptible to infection by certain subgroups of avian retroviruses. Different avian cell lines are susceptible to different subgroups of avian retroviruses. Subgroup A (strain SRA) replicates well in CHCC-OU2 cells, whereas subgroups B (strain SRB) and D (strain SRD) replication is barely detectable and those of subgroup C (strain BH-RSV (RAV-7)) and E (strain QV2f) do not replicate in CHCC-OU2 cells.

The MDV-OCL, FC126-OCL and SB1-OCL cell lines display the same growth characteristics as the parental CHCC-OU2 cell line. While these cells harbor MDV virus, they are not transformed and do not induce tumors when injected into birds. These cell lines, when sub-confluent have all of the same morphological characteristics as the parental CHCC-OU2 cells. Production of infectious virus in the FC126-OCL cell line begins when the cell monolayer has reached a cell density wherein each cell is in contact with its neighbor, approximately within the range of $4 \times 10^4$ to $6 \times 10^4$ cells/cm$^2$. The development of CPE and production of infectious virus is very rapid and is complete within two days of cell contact. On the other hand, the SB1-OCL and MDV-OU2 cell lines do not produce CPE and infectious virus until three to four days after the cell monolayer has reached a density within the approximate range of $6 \times 10^4$ to $1 \times 10^5$ cells/cm$^2$. Expression of FC126 and SB1 virus from their respective cell lines is dependent on the cell lines reaching a cell culture density of more than 50% confluence before expression of virus is detected.

The MDV infected cell lines can be used to produce a vaccine. The MDV infected cell lines can also be used to test various agents or conditions which suppress or enhance cell responses, such as stimulating class 1 major histocompatibility complex molecule production and thereby stimulating a cell-mediated response to MDV.

The preferred MDV virus is selected from serotypes 1, 2 and 3. Serotype 3 is referred to as turkey herpesvirus (HVT). The MDV can be a recombinant virus comprising foreign genes or a deletion mutant which is used as a vaccine or for other uses. The MDV can also be a defective virus comprising an origin of replication and foreign DNA sequences.

The present invention particularly relates to sustainable chick cell line (FC126-OCL) stably infected with HVT strain FC126 and sustainable chick cell line (SB1-OCL) stably infected with serotype 2 MDV strain SB1. FC126-OCL and SB1-OCL cell lines grow continuously in culture and, once confluent, display plaques characteristic of MDV infection. FC126-OCL and SB1-OCL can be used separately or together as a vaccine to provide immunity in avians against pathogenic strains of MDV. The FC126-OCL and SB1-OCL cells have remained viable and continue to produce MDV after cryogenic storage and continuous culture.

As shown in the examples, the cell lines are infected with MDV. Presence of distinct plaques in confluent monolayers is consistent with cytolytic restrictive productive infection, similar to that observed in primary CEF. The titer of infectious virus produced by the cell lines when confluent increased after each cell culture passage, as expected from replication of cell lines that harbored MDV. The cell lines are capable of transferring MDV infection to primary CEF cultures, to uninfected CHCC-OU2 cells, and to avians. Finally the cell lines are able to confer protection to avians against pathogenic strains of MDV such as serotype 1 MDV strain GA passage 8 and Md11p15.

Master stocks of sustainable MDV vaccine cell lines are created from multiple large cultures of CHCC-OU2 cells infected with either cultures of the sustainable MDV vaccine cell lines or MDV infected CEF. When virus plaques become evident, these cultures are harvested by trypsinization, or scraping of culture vessels and the MDV infected cells are passed to new cultures. The culture passages are repeated until cultures are created where the majority of CHCC-OU2 cells are infected with MDV vaccine. In this manner, sustainable MDV vaccine cell lines are made that can serve as the master seed stocks for MDV vaccine production. These master seed stocks can be validated for MDV vaccine use by the U.S. Department of Agriculture. When MDV vaccine infected CEF are used as the starting material the number of passages must be increased such that the cells have been in culture for three weeks to ensure that all CEF which have a life span of approximately two weeks have died.

An alternative method for making sustainable MDV vaccine master seed stocks is to transfect CHCC-OU2 cells with DNA comprising the vaccine virus genome into the CHCC-OU2 cells. The method of transfection comprises any of the techniques described in J. Seabrook, et al., In "molecular cloning: a laboratory manual", 2nd Ed Cold Spring Harbor Laboratory, Cold Spring Harbor, N.Y. (1989) pp. 16.30–16.55 used to transfect DNA into cells, such as calcium phosphate precipitation, polybrene, DEAE-dextran, LIPOFECTIN, electroporation, or protoplast fusion. DNA transfection is especially useful in the preparation of master seed stocks of genetically engineered virus vectors or defective virus vectors.

A further alternate method for making Master seed stocks of sustainable MDV vaccine cell lines is by cell culture expansion of infected cell populations. A culture of CHCC-OU2 cells is infected with MDV by any method described herein at a low multiplicity of infection. When plaques become evident a plaque is removed from the infected CHCC-OU2 culture and transferred to a tissue culture dish not containing any cells. The cells are cultured until the culture has approached confluence. The culture is harvested by trypsinization, the MDV infected cells concentrated by low speed centrifugation, and passed to a larger tissue culture dish. The cells are again cultured until the culture has approached confluence. The cells are harvested as above and transferred to a larger tissue culture dish. By this manner the majority of the cells are infected and all of the infected cells were derived from one MDV plaque. The production of infectious MDV can be accomplished during any stage of the expansion of the MDV infected cell line simply by letting the culture reach confluence.

The use of MDV-OCL cell lines for production of MDV vaccines is as follows. Master seed stocks of MDV-OCL cell lines are cultured at subconfluent density. MDV remains in a latent state in the dividing cells until the culture reaches confluent levels, wherein the virus infection becomes productive. When infection has progressed to be visually evident, usually two days post-confluence, the cells are harvested by techniques common to those skilled in the art of MDV vaccine production (A. E. Churchill, "Marek's Diseases: Scientific Basis and Methods of Control: Production of Vaccines." (L. N. Payne, Ed.), Martinus Nijoff Publishing, Boston, Mass., pp. 251–266. (1985)). Typically, preparation of infected cells for MDV vaccines involves the following steps 1), cells are trypsinized or scraped from the culture support, 2) the productively infected cells are concentrated by low speed centrifugation, and 3) the infected cells, now concentrated, are resuspended in an appropriate volume of diluent to produce a vaccine with a defined concentration of MDV plaque forming units per milliliter (PFU/ml). Preferably, continual MDV vaccine production is achieved by arranging multiple cultures of MDV-OCL cell lines from the master seed stock in a series, with each successive culture in the series at a sub-confluent level that is less than the preceding culture. For example, cultures are set up at sub-confluent levels of 90%, 80%, 70%, 60%, and 50%. When the 90% culture reaches confluence, MDV infection is productive and the culture is harvested for MDV vaccine and a new culture is set up from the master stock at 50% confluence. In this manner, continual production of MDV vaccines can be achieved.

An alternative and equally effective method for producing MDV vaccine is to maintain cultures of uninfected CHCC-OU2 cells. These cultures are infected with appropriate MDV-OCL cell line master seed stock. This method is similar to the current method use to produce MDV vaccine from CEF (A. E. Churchill, "Marek's Diseases: Scientific Basis and Methods of Control: Production of vaccines." (L. N. Payne, Ed.), Martinus Nijoff Publishing, Boston, Mass., pp. 251–266 (1985)).

EXAMPLE 1

Cells and Virus

Preparation, propagation, and infection of CEF cells with HVT were performed as described previously (C. Glaubiger et al., J. Virol. 45:1228–1234 (1983); P. M. Coussens and L. F. Velicer, J. Virol. 62:2373–2379 (1988)). The HVT vaccine strain FC126 used in this study was at cell culture passage level 10 (FC126p10) The serotype 2 vaccine strain SB1 used in this study was at cell culture passage level 29 (SB1p29) CHCC-OU2 cells (H. Ogura and T. Fujiwara, Acta Med. Okayama 41:141–143 (1987)) were obtained from Dr. Donald Salter, Avian Disease and Oncology Laboratory (ADOL), U.S. Department of Agriculture (USDA), East Lansing, Mich., and were cultured in Leibovitz L15-McCoy 5A (LM) (Gibco, Grand Island, N.Y.) media supplemented with 10% calf serum and 2% tryptone phosphate broth (TPB) at 37° C. in a humidified atmosphere containing 5% $CO_2$.

EXAMPLE 2

MDV-OU2 Serotype 1 Cell Line Infection of CHCC-OU2 Cells with Md11p5:

As shown in application Ser. No. 08/549,045, CHCC-OU2 cells were infected with MDV strain MD11 cell culture passage 15 (MD11p5) by combining $5.0 \times 10^7$ CHCC-OU2 cells with $2.0 \times 10^7$ Md11p15 infected CEF prior to plating on 150 mm culture dishes in LM medium supplemented with 4% calf serum (CS). Co-cultivation of CHCC-OU2 cells with Md11 infected CEF cells was continued for four passages. Cells from each of these passages have been preserved at $-135°$ C. in freezing media (LM media (Life Technologies, Gaithersburg, Md.) supplemented with 20% CS and 10% dimethyl sulfoxide). At four passages post-infection, numerous plaques (approximately 100 plaques per 150 mm culture dish), characteristic of MDV infections in CEF cells, were observed. Two of these plaques were isolated using sterile cloning cylinders. Cylinders were placed on top of individual plaques, cells were trypsinized and aspirated from the cloning cylinders. Aspirated cells were transferred to 35 mm culture dishes containing LM media supplemented with 4% CS for expansion. During expansion, cells were not allowed to become confluent and media was changed every 48 to 72 hours. Expanded clones were designated MDV OU2.1 and MDV OU2.2.

During purification of MDV OU2. 1 and MDV OU2.2 CPE was slow in developing and expanding. Fully developed plaques consisting of syncytia and extended regions of rounded, loosely attached, cells were not visible until four weeks post-infection. The appearance of visible plaques 14 days post-infection and the dependence of plaque formation on the cells reaching confluence and contact inhibition was not expected. By comparison, a typical CEF monolayer infected with MDV strain Md11 will develop readily visible plaques in 5–7 days post-infection with complete destruction of the monolayer within 10–14 days. Plaque formation in CEF is independent of the confluence of the cell monolayer. After four weeks of co-cultivation, cells were cryogenically preserved at $-135°$ C. for two weeks. Cell cultures were re-established from frozen cells by combining infected (Md11p15/OU2) and uninfected CHCC-OU2 cells. Plaques consistent with MDV infection were not observed until cells reached confluence, approximately 14 days post-plating.

EXAMPLE 3

FC126-OCL Cell Lines

For FC126-OCL.1, passage 0 was from an infection of a 100 mm tissue culture dish of confluent CHCC-OU2 with $2.5 \times 10^6$ PFU FC126 passage 10 (FC126p10) infected CEF. When CPE became evident the infected cells were harvested and frozen in freezer storage buffer comprising 10% DMSO, 20% calf serum in 5% LM (FSB) at $-135°$ C. (passage 0). A $10^{-2}$ dilution of the infected frozen cells was used to infect a well of a 24-well tissue culture dish of confluent CHCC-OU2. After CPE had become near 100%, cells were frozen in FSB at $-135°$ C. (passage 1). After storage at $-135°$ C., the cells were thawed and used to infect three wells of confluent CHCC-OU2 in a 24-well tissue culture dish at $10^{-1}$, $10^{-2}$, and $10^{-3}$ dilution (passage 2). The three dilutions were pooled and replated to the well of a 12-well tissue culture plate (passage 3). When cells became confluent, and CPE became evident, the infected cells were harvested and divided between two wells of a 12-well tissue culture dish (passage 4). When CPE became evident, cells were harvested from both wells and pooled. 0.1 ml was removed and used to infect one well of a 12-well tissue culture dish (passage 5). When CPE became evident the cells were harvested and frozen in FSB at $-135°$ C. The frozen cells were then used to infect a 100 mm tissue culture dish of confluent CHCC-OU2 (passage 6). When CPE became evident the cells were harvested, one tenth the sample was removed to determine PFU/ml for passage 5 and the rest of the infected cells were replated to a 100 mm tissue culture dish (passage 6). When CPE became evident the cells were harvested, one tenth the sample was removed to determine PFU/ml for passage 7 and the rest of the infected cells were replated to a 100 mm tissue culture dish (passage 8). When CPE became evident the cells were harvested, one tenth the sample was removed to determine PFU/ml for passage 8 and the rest of the infected cells were frozen in FSB at $-135°$ C. as FC126-OCL.1.

For FC126-OCL.2, passage 0 was from an infection of a well of a 24-well tissue culture dish of confluent CHCC-OU2 with $3.75 \times 10^3$ PFU of FC126p10 infected CEF. After CPE had become 100%, cells were frozen in FSB at $-135°$ C. After storage at $-135°$ C., the cells were thawed and used to infect three wells of confluent CHCC-OU2 in a 24-well tissue culture dish at $10^{31\ 1}$, $10^{-2}$ and $10^{-3}$ dilution (passage 1). The three dilutions were pooled and replated to the well of a 12-well tissue culture plate (passage 2). When cells became confluent, CPE became evident and 55 plaques were counted. The infected cells were harvested and divided between two wells of a 12-well tissue culture dish (passage 3). When CPE became evident, cells were harvested from both wells and pooled. The approximate titer was $5.5 \times 10^3$ PFU/ml. 0.1 ml was removed and used to infect one well of a 12-well tissue culture dish (passage 4). When CPE became evident the cells were harvested and frozen in FSB at $135°$ C. The frozen cells were then used to infect a 100 mm tissue culture dish of confluent CHCC-OU2 (passage 5). When CPE became evident, the cells were harvested, one tenth the sample was removed to determine PFU/ml for passage 5 and the rest of the infected cells were replated to a 100 mm tissue culture dish (passage 6). When CPE became evident the cells were harvested, one tenth the sample was removed to determine PFU/ml for passage 6 and the rest of the infected cells were replated to a 100 mm tissue culture dish (passage 7). When CPE became evident the cells were harvested, one tenth the sample was removed to determine PFU/ml for passage 7 and the rest of the infected cells were frozen in FSB at $-135°$ C. as FC126-OCL.2.

The method for generating HVT infected CHCC-OU2 cells (FC126-OCL.3). CHCC-OU2 cell confluent monolayer containing $20 \times 10^6$ CHCC-OU2 cells on a 150 mm culture dish were infected with $2 \times 10^6$ PFU of FC126p10infected CEF. After three days of cultivation, numerous plaques, characteristic of viral infection were observed. The infected cells were trypsinized and transferred to a sterile 150 mm culture dish. One tenth of the cells were reserved to determine the number of PFU. The designated passage 1 infected cells were further cultivated for two days and then trypsinized and transferred to a sterile 150 mm culture dish with one tenth reserved to determine the number of PFU. The passage 2 infected cells were further cultivated for one day and then trypsinized and transferred in equal aliquots to two sterile 150 mm culture dish. One tenth was reserved to determine the number of PFU and one-fifth was preserved at $-135°$ C. in FSB. The proportion of infected cells (or PFU) was increased by each serial passage of the infected cells in the previously described manner.

While three different methods for generating the FC126-OCL cell lines have been described and the resultant cells from each of the three methods has been designated FC126-OCL.1, FC126-OCL.2 and FC126-OCL.3, respectively, the three cell lines are substantially the same since all three were created with the same stock of FC126p10infected CEF. Only the passage levels and cultivation techniques varied slightly. The slight variation in cultivation between the three cell lines was not expected to render the three cell lines distinct. The cell line designations are only for convenience of tracking the experiments and do not reflect differences in the biological properties of the FC126 virus in the three cell lines. The three methods illustrate that MDV cell lines can be constructed regardless of the precise method used. All three cell lines can be represented by the generic designation FC126-OCL.

EXAMPLE 4

SB1-OCL Cell Line

The method for generating SB1 infected CHCC-OU2 (SB1-OCL.1) was the same as the method described for generating FC126-OCL.3. A CHCC-OU2 cell confluent monolayer containing $20 \times 10^6$ CHCC-OU2 cells on a 150 mm culture dish was infected with $3 \times 10^5$ PFU of SB1 passage 29 (SB1p29) infected CEF. After three days of cultivation, numerous plaques, characteristic of viral infection were observed. The infected cells were trypsinized and transferred to a sterile 150 mm culture dish. One tenth of the cells were reserved to determine the number of PFU. The designated passage 1 infected cells were further cultivated for two days and then trypsinized and transferred to a sterile 150 mm culture dish with one tenth reserved to determine the number of PFU. The passage 2 infected cells were further cultivated for one day and then trypsinized and transferred in equal aliquots to two sterile 150 mm culture dish. One tenth was reserved to determine the number of PFU. The proportion of infected cells (or PFU) were increased by serial passage of the infected cells in the previously descried manner. By the previously described manner SB1-OCL stocks at passage levels 3, 4 on up to 20 have been made.

EXAMPLE 5

Determination of Virus Titers for HVT-OCL and SB1-OCL Cell Lines

Determination of PFU for FC126-OCL cell lines.1, .2, and .3 and SB1-OCL.1 was done by cultivating serial dilutions of the one tenth reserved samples from each passage level onto CEF. The serial dilutions were made in LM containing 4% calf serum and the dilutions were in 10-fold increments and ranged from $10^{-1}$ to $10^{-7}$.

Table 1 shows the increase in titers for cell lines FC126-OCL.1 and FC126-OCL.3 for tissue culture passages 5, 6, 7, and 8 and the first three passages for cell lines FC126-OCL.2 and SB1-OL.1. An increase in titers after each culture passage represents an enrichment for cell lines containing virus since the passages were made from replating infected cells onto empty tissue culture dishes and not simply infecting tissue culture dishes of uninfected cells. After the initial infection with high titer stock of FC126 infected CEF, no CEF would be expected to survive the subsequent passages in cell line purification for several reasons. 1) CEF have a finite life span and do not persist in tissue culture for more than two or three weeks, therefore any uninfected CEF would not be expected to persist more than two weeks beyond the initial infection of CHCC-OU2. 2) The initial infection of CHCC-OU2 was with infected CEF at near 100% CPE. At 100% CPE every cell is infected and the infected cells have begun to detach from the tissue culture dish. Replating CEF at that point of infection would not establish a monolayer, and 3) CEF are very sensitive to freeze-thawing and do not usually survive several rounds of 
freeze-thawing. The PFU/ml for the FC126-OCL.3 cell line is two orders of magnitude greater than PFU/ml attainable for FC126 propagated on CEF. The PFU/ml of SB1-OCL.1 is one order of magnitude greater than the PFU/ml attainable by SB1 propagated on CEF. The maximum PFU/ml for both cell lines has not been determined.

TABLE 1

| Passage Level | FC126-OCL.1 (PFU/ml) | FC126-OCL.2 (PFU/ml) | Passage Level | FC126-OCL.3 (PFU/ml) | SB1-OCL.1 (PFU/ml) |
|---|---|---|---|---|---|
| 5 | ND | $3.5 \times 10^3$ | 0 | $1.6 \times 10^6$ | $3.6 \times 10^5$ |
| 6 | $1 \times 10^4$ | $3.0 \times 10^5$ | 1 | $4.2 \times 10^5$ | $3.2 \times 10^5$ |
| 7 | $8.5 \times 10^5$ | $1 \times 10^6$ | 2 | $3.0 \times 10^6$ | $8.7 \times 10^5$ |
| 8 | $0.9 \times 10^6$ | ND | 3 | $4.5 \times 10^8$ | $1 \times 10^6$ |

EXAMPLE 7

Comparison of FC126-OCL.1 to Conventional FC126 Vaccine.

The ability of the sustainable cell line containing the commercial HVT vaccine strain FC126 (FC126-OCL) to protect chickens against MDV was compared to HVT vaccine strain FC126 (FC126-CEF) propagated on CEF, the current method for producing MDV vaccines. This experiment compared the efficacy of FC126-OCL to protect day-old chicks when given at the same dosage level recommended for current FC126 vaccines.

Four groups of one-day old chicks (specified pathogen free and MDV susceptible chicks from SPAFAS, Chicago, Ill.) were vaccinated with: 1) 2,000 PFU of FC126-OCL at cell culture passage 17 (16 chicks), 2) 2,000 FC126-CEF at cell culture passage 10 (16 chicks), and 3) uninfected OCL at same cell concentration as FC126-OL (10 chicks). A fourth group of 10 chicks served as a control. At day seven post-vaccination, 13 chicks from groups 1 and 2, and 8 chicks from groups 3 and control were challenged with 2,000 PFU of virulent MDV strain GA. At 32 days post-challenge, the chicks were necropsied for pathological signs of MDV infection. MDV pathological expression is manifest as gross lesions of the peripheral nervous system, presence of lymphoid tumors in a variety of organs such as the gonads, liver kidney, heart, and spleen and atrophy of the bursa of Fabricious.

Both birds inoculated with the uninfected cell line and the controls had numerous pathologic indications of MDV infection. Significantly, none of the chicks vaccinated with the FC126-OCL cell line, and challenged with MDV, had any pathologic evidence of MDV infection. The result of the efficacy experiment is presented in Table 2. The experiment demonstrates that vaccination with FC126-OCL, at dosage levels equivalent to recommended commercial dosages for FC126-CEF, protects chickens against MDV as well as traditional CEF propagated FC126.

TABLE 2

| | Protective Efficacy | |
|---|---|---|
| Vaccine[1] | Protection[3] | Protective Index[4] |
| FC126-OCL | 13/0 | 100 |
| FC126-CEF | 13/0 | 100 |
| OCL Cells[2] | 2/8 | — |
| Control | 1/8 | — |

[1] Chicks vaccinated at day one with 2000 PFU.
[2] Chicks inoculated with OCL cells equivalent to number of cells in 2000 PFU FC126-OCLlpl7.
[3] All chicks challenged at day seven post-vaccination with 2000 PFU MDV strain GA. Experiment terminated at day 32 post-challenge. Protection marked as absence of signs of MDV by necropsy.
[4] Protective index: % MD in controls - % MD in vaccinates/% MD in controls × 100.

EXAMPLE 8

Stability of MDV in Cell Lines

After 31 passages of the MDV-OU2 cell lines viral DNA was analyzed by PCR for expansion of the het region. Unexpectedly, no expansion of the het region was observed. Therefore, unlike MDV propagation in CEF, MDV is stabilized in the present invention therefore enabling MDV cell lines can be propagated indefinitely without risk of reduction in vaccine efficacy.

PCR was used as an assay to estimate the number of the 132-bp DR sequence in the MDV OU2.2 and OU2.1 after serial passage in cell culture.

Total cellular DNA was extracted from CEF infected with Md11 cell culture passage 14, CEF infected with MD11 cell culture passage 48, and MDV-OU2.2 cell culture passage 48 by standard methods (J. Sambrook, et al., in "Molecular cloning: a laboratory manual", 2nd ed. Cold Spring Harbor Laboratory, Cold Spring Harbor, N.Y. (1989) pp. 9.16–9.19) and used as templates for PCR amplification of the 132-bp DR sequences. The upstream oligonucleotide primer was 5'-TGCGATGAAAGTGCTATGGAGG-3' (SEQ ID NO:1). The downstream oligonucleotide primer was 5'-GAGAATCCCTATGAGAAAGCGC-3' (SEQ ID NO:2). The upstream primer is 3 bp 5' to the DR sequence. The downstream primer is 6 bp downstream from the 3' end of the DR sequence. The two primers amplify a 317 bp fragment in the case of two copies of the DR sequence (R. F. Silva, Avian Dis. 36:521–528 (1992)). The PCR conditions were slightly modified from the original conditions (R. F. Silva, Avian Dis. 36:521–528 (1992)). Briefly, 500 nanograms of total cellular DNA was mixed with 20 mM of each dNTPs, 20 $\mu$M of each oligonucleotide primer pair, 10 $\mu$l 10× PCR reaction buffer (GIBCO BRL, Life Technologies, Gaithersburg, Md.), 1.5 mM $MgCl_2$, and 1.0 U Taq polymerase (GIBCO BRL, Life Technologies, Gaithersburg, Md.). The PCR reactions were performed using a GeneAmp 9600 thermal cycler (Perkin Elmer Cetus, Norwalk, Conn.). Following an initial denaturing step at 95° C. for 5 minutes, the DNA was amplified during 25 cycles of 95° C. for 45 seconds. 67° C. for 45 seconds, and 72° C. for 45 seconds. The PCR reaction was completed by a final elongation step at 72° C. for 10 minutes. PCR product was analyzed on 6% polyacrylamide gels, stained with ethidium bromide, and photographed under ultraviolet light. Sizes of amplified fragments were determined by comparison to 1 kb DNA ladder (GIBCO BRL, Life Technologies, Gaithersburg, Md.).

In all reactions it is possible to see a 185 bp amplified fragment that corresponds to one copy of the 132-bp DR

Figure 1A:
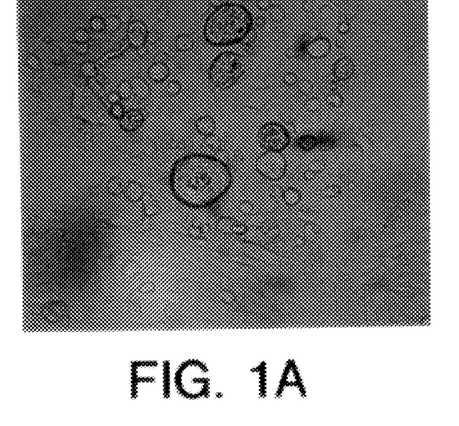
FIGS. 1A to 1D are photomicrographs of FC126-OCL and SB1-OCL. Monolayer cultures of FC126-OCL display plaques consisting of a mixture of several large infected cells and numerous smaller infected cells (FIG. 1A) whereas FC126 plaques on CEF consist of infected cells of uniform size (FIG. 1B). Monolayer cultures of SB1-OCL display plaques consisting of large infected cells (FIG. 1C) whereas SB1 plaques on CEF consist of small infected cells (FIG. 1D).
Figure 1B:
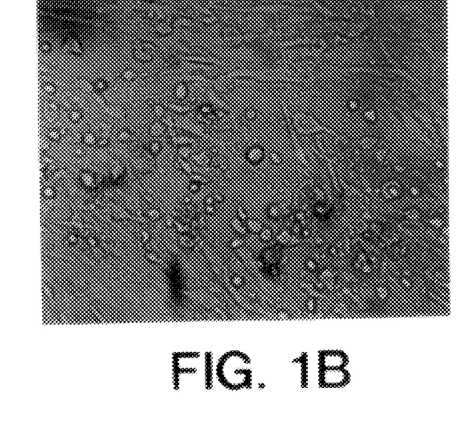
Figure 1C:
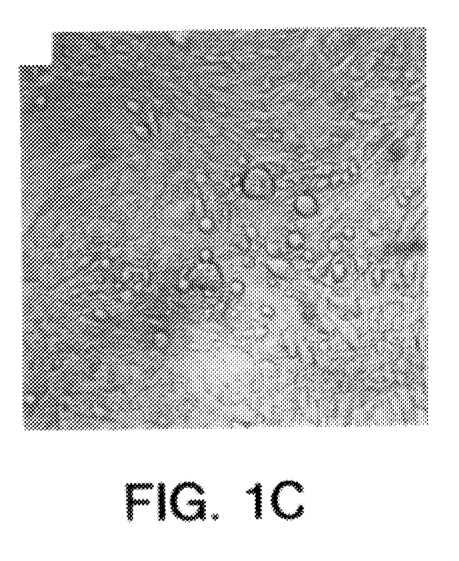
Figure 1D:
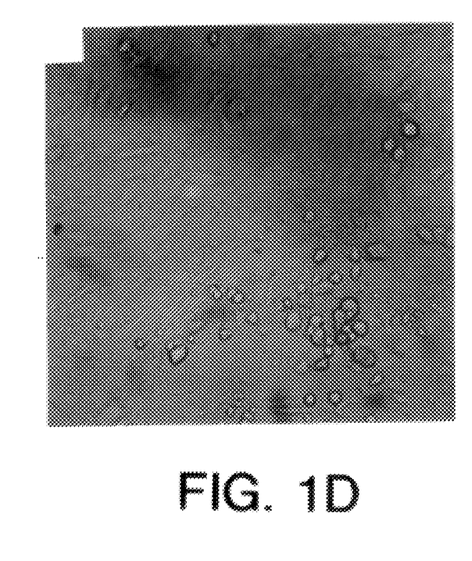
Figure 2:
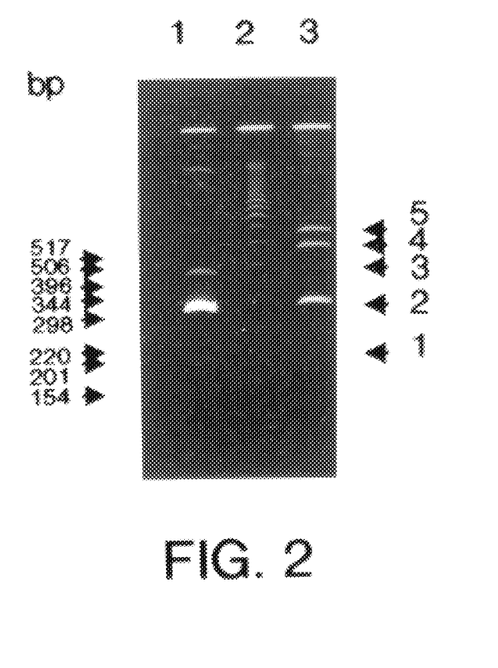
FIG. 2 is a PCR amplification of the 132-bp DR sequence. DNA isolated from Md11 passage 14 (lane 1), Md11 passage 48 (lane 2), and MDV-OU2.2 passage 48 (lane 3) were used for PCR amplification. Numbered arrows on the right indicate positions of DR fragments with one to five copies of the 132-bp DR sequence. Arrows on the left represent positions of selected bands from the 1 kb DNA ladder marker (GIBCO BRL, Life Technologies, Gaithersburg, MD).

(FIG. 2). However, characteristic of pathogenic MD11, a 317 bp fragment corresponding to two copies of the 132-bp DR is predominant for MD11 passage 14 (FIG. 2, lane 1). This 317 bp fragment is no longer present in MD11 attenuated by passage 48 (FIG. 2, lane 2). Significantly, MDV OU2.2 at passage 48 still maintains the 317 bp fragment characteristic of pathogenic MD11 (FIG. 2, lane).

Results of PCR analyses indicate that MDV in MDV OU2.2 and OU2.1 (data not shown) cell lines is not attenuated after 48 serial in vitro passages. In contrast, and as expected, MD11 after 48 serial in vitro passages on CEF is attenuated. These results indicate that MDV is stably maintained during in vitro propagation in CHCC-OU2 cells. This unexpected observation is of great importance to MDV vaccine producers because the present invention enables vaccine viruses to be propagated in vitro indefinitely or at least for 48 cell passages. This is in contrast to propagation of vaccine strains of MDV on CEF where in vitro passages results in loss of protective efficacy. Typically vaccine strains of MDV can be propagated on CEF only 5 passages beyond the master seed stock. Each passage beyond 5 must be demonstrated to be as efficacious as the 5th passage before receiving U.S. Department of Agriculture approval for licensing. Once demonstrated to the U.S. Department of Agriculture, the present invention will enable vaccine strains to be propagated indefinitely beyond the master seed stock without requalifying each passage beyond the 5th passage.

The following Examples show the characteristics of CHCC-OU2 cells. These characteristics are the same for MDV infected cells.

EXAMPLE 9

The technique of B. F. Benkel et al (Poultry Science 71:1520–1526 (1992)) was used to demonstrate that CHCC-OU2 cells were homozygous for ev1. Total cellular DNA was extracted from CHCC-OU2 cells and avian cells containing ev1, ev1 and ev6, or ev15 by standard methods in J. Sambrook, et al., in "Molecular Cloning: a laboratory manual", 2nd ed. Cold Spring Harbor Laboratory, Cold Spring Harbor, N.Y. (1989) pp. 9.16–9.19. Total cellular DNA was used as templates for PCR amplification using a primer set consisting of primers PR-A (5'-GCACCAAACAATCTAGTCTGTGC), PR-B (5'-AAGTACTCACTTCTCTGAAC), and PR-C (5'-GCCAAGCTTCAATGAAGCAGAAGGCTTC) SEQ ID NO:3, SEQ ID NO:4 and SEQ ID NO:5, respectively. Primer PR-A is specific for the genomic region upstream of the ev1 insert, primer PR-B is specific for the genomic region downstream of the ev1 insert and primer PR-C is specific for the ev1 long terminal repeat. PCR of DNA from a bird homozygous for ev1 with these primers will produce DNA fragments 300 bp in length. PCR of DNA from a bird heterozygous for ev1 with these primers will produce DNA fragments of 300 bp and 510 bp whereas PCR of DNA from a bird lacking ev1 will produce DNA fragments of 510 bp. The PCR reactions were performed as described in B. F. Benkel et al (Poultry Science 71:1520–1526 (1992) using a GeneAmp 9600 thermal cycler (Perkin Elmer Cetus, Norwalk, Conn.). The PCR products were analyzed by electrophoresis on 1% agarose gels stained with ethidium bromide and photographed under ultraviolet light (J. Sambrook, et al., in "Molecular Cloning: a laboratory manual", 2nd ed. Cold Spring Harbor Laboratory, Cold Spring Harbor, N.Y. (1989) pp. 6.2–6.19). Sizes of amplified products were determined by comparison to 1 kb DNA ladder (GIBCO BRL, Life Technologies, Gaithersburg, Md.). In FIG. 3, CHCC-OU2 cells produce a single product of 300 bp indicating CHCC-OU2 cells are homozygous for ev1. The heterozygous ev1, and ev1 and ev6, positive control DNAs produced two products of 300 bp and 510 bp. The negative control ev15 DNA produced only one product of 510 bp, expected for DNA not containing ev1.

The technique of B. F. Benkel and E. J. Smith (Poultry Science 72:1601–1605 (1993)) was used to demonstrate that CHCC-OU2 cells were homozygous for ev15. Total cellular DNA from CHCC-OU2 cells and avian cells containing ev1 or ev1 S were used as templates for PCR amplification using a primer set consisting of primers 15-1 (5'-CAAATGAGGGTAATAAGGGAG) and 15-2 (5'-CACTACCAAATATAATTCTGTAG), SEQ ID NO:6 and SEQ ID NO:7, respectively. Primer 15-1 is specific for the genomic region upstream of the ev15 insert and primer PR-15 is specific for the genomic region downstream of the ev15 insert. PCR of DNA from a bird homozygous for ev15 with these primers will produce DNA fragments 434 bp in length. PCR of DNA from a bird heterozygous for ev15 with these primers will produce DNA fragments of 434 bp and 181 bp whereas PCR of DNA from a bird lacking ev15 will produce DNA fragments of 181 bp. The PCR reactions were performed as described in B. F. Benkel and E. J. Smith (Poultry Science 72:1601–1605 (1993)) using a GeneAmp 9600 thermal cycler (Perkin Elmer Cetus, Norwalk, Conn.). The PCR products were analyzed by electrophoresis on 1% agarose gels stained with ethidium bromide and photographed under ultraviolet light (J. Sambrook, et al., in "Molecular Cloning: a laboratory manual", 2nd ed. Cold Spring Harbor Laboratory, Cold Spring Harbor, N.Y. (1989) pp. 6.2–6.19). Sizes of amplified products were determined by comparison to 1 kb DNA ladder (GIBCO BRL, Life Technologies, Gaithersburg, Md.). In FIG. 4, CHCC-OU2 cells produce a single product of 434 bp indicating CHCC-OU2 cells are homozygous for ev15. The heterozygous ev15, positive control DNA produced two products of 434 bp and 181 bp. The negative control ev1 DNA produced only one product of 181 bp, expected for DNA not containing ev15.

A continuous cell line that can support MDV replication and be used for production of MDV vaccines has tremendous economic implications for the poultry industry. The advantages of such a cell line are: 1) The cell line would substantially reduce costs associated with producing MDV vaccines by eliminating the need for a continuous supply of fertile eggs from SPF flocks, reducing the risk of vaccine production loss due to a disruption of SPF egg supplies, and eliminating the effect of price variations for fertile SPF eggs; 2) Validation of master cell stocks would be possible, and thereby avoid risks associated with preparing each batch of CEF cells; 3) CHCC-OU2 cells infected with vaccine strains of MDV can be propagated indefinitely, and production of virus can be induced by allowing infected cells to reach confluence; 4) The same manufacturing techniques used for producing MDV vaccines from CEF cells can be used with CHCC-OU2 cells. 5) MDV is stabilized in the cell lines. Reduced costs would benefit poultry producers and consumers. In the present invention, sustainable cell lines that produce MDV and are used as vaccines to protect avians against Marek's disease is claimed.

It is intended that the foregoing descriptions be only illustrative of the present invention and that the present invention be limited only by the hereinafter appended claims.

We claim:

1. An immortal Marek's disease virus (MDV) infected chicken cell line which consists of chick embryo cells (CEC) which are chicken helper factor (Chf) negative and virus-free and which have been treated with a chemical mutagen to render the CEC cells immortal and then are infected with MDV and maintained over time as a monolayer, wherein the immortal MDV infected cell line is able to transfer infectious MDV to avians in vivo, and wherein the MDV infection can be maintained as a non-lytic or a lytic infection.

2. The cell line of claim 1 wherein the MDV is a virus used for the preparation of a virus vaccine to produce immunity in the avian.

3. The cell line of claim 1 wherein the MDV is selected from the group consisting of Turkey herpesvirus (HVT) strain FC126 deposited in cell line ATCC CRL 12052 and Marek's Disease Virus (MDV) strain SB1 deposited in cell line CRL 12053.

4. The cell line of any one of claims 1 or 2 wherein the MDV is a virus selected from the group consisting of serotype 1, serotype 2, and serotype 3 MDV, wherein serotype 3 is a turkey herpesvirus (HVT).

5. The cell line of any one of claims 1 or 2 wherein the MDV is genetically engineered comprising one or more foreign genes inserted into one or more sites in the MDV.

6. The cell line of any one of claims 1 or 2 wherein the immortal MDV infected cell line comprises a genetically engineered MDV having one or more MDV genes deleted.

7. The cell line of any of claims 1, 2, or 3 wherein the CEC are CHCC-OU2 cells deposited as ATCC CRL-12302.

8. The cell line of any one of claims 1, 2 or 3 wherein the MDV infection can be converted to a lytic infection by cell stress or contact inhibition.

9. A method for producing an immortal Marek's disease virus (MDV) infected chicken cell line in a non-confluent monolayer culture which comprises:
   (a) combining chick embryo cells (CEC) which are chicken helper factor free and virus-free and which have been treated with a chemical mutagen to render the CEC cells immortal with MDV in a culture medium so that the CEC are infected with MDV; and
   (b) purifying the MDV infected CEC; and
   (c) propagating the MDV infected CEC to produce the cell line in a monolayer culture, wherein the MDV infection can be maintained as a non-lytic or a lytic infection.

10. The method of claim 9 wherein MDV is selected from the group consisting of cell-associated MDV derived from primary embryo fibroblasts, cell-free MDV, and MDV DNA transfected into the immortal CEC.

11. The method of any one of claims 9 or 10 wherein the immortal MDV infected cell line is for the preparation of a vaccine to produce immunity in the avian.

12. The method of any one of claims 9 or 10 wherein the MDV is a virus selected from the group consisting of serotype 1, serotype 2, and serotype 3 MDV, wherein serotype 3 is a turkey herpesvirus (HVT).

13. The method of any one of claims 9 or 10 wherein the MDV is genetically engineered comprising one or more foreign genes inserted into one or more sites in the MDV.

14. The method of any one of claims 9 or 10 wherein the immortal MDV infected cell line comprises a genetically engineered MDV having one or more MDV genes deleted.

15. The method of any one of claims 9 or 10 wherein the MDV is selected from the group consisting of Turkey herpesvirus (HVT) strain FC126 infected cell line deposited as ATCC CRL-12052 and MDV strain SB1 infected cell line deposited as ATCC CRL-12053.

16. The method of any one of claims 9 or 10 wherein the CEC cells are CHCC-OU2 cells deposited as ATCC CRL-12302.

17. An immortalized Marek's disease herpesvirus cell line deposited as ATCC CRL 12052 containing Marek's disease Turkey herpes virus (HVT) strain FC126.

18. An immortalized Marek's disease herpesvirus cell line deposited as ATCC CRL 12053 containing Marek's Disease (MDV) serotype 2 strain SB1.

19. An immortal Marek's disease virus (MDV) infected chicken cell line in a monolayer culture which consists of chick embryo cells (CEC) which are chicken helper factor negative and non-malignant and contain DNA sequences from avian retroviruses and which grows continuously in a cell culture.

20. The cell line of claim 19 wherein the MDV is a virus used for the preparation of a virus vaccine to produce immunity in the avian.

21. The cell line of any one of claims 19 or 20 wherein the MDV is genetically engineered comprising one or more foreign genes inserted into one or more sites in the MDV.

22. The cell line of any one of claims 19 or 20 wherein the immortal MDV infected cell line comprises a genetically engineered MDV wherein one or more MDV genes are deleted.

23. The cell line of any one of claims 19 or 20 wherein the CEC are CHCC-OU2 cells deposited as ATCC CRL-12302.

24. The cell line of any one of claims 19 or 20 wherein the MDV infection can be converted to a lytic infection by cell stress or senescence.

25. A method for producing an immortal Marek's disease virus (MDV) infected chicken cell line which comprises:
 (a) combining chick embryo cells (CEC) which are chicken helper factor free and virus-free and which have been treated with a chemical mutagen to render the CEC cells immortal with the MDV in a culture medium so that the CEC are infected with MDV; and
 (b) purifying the MDV infected CEC; and
 (c) propagating the MDV infected CEC to produce the cell line.

26. The method of claim 25 wherein the CEC cells are CHCC-OU2 cells deposited as ATCC CRL-12302.

27. The method of claim 25 wherein the MDV used to make the cell line is selected from the group consisting of serotype 1 MDV, serotype 2 MDV, or serotype 3 MDV, wherein serotype 3 MDV is turkey herpesvirus.

28. The method of claim 25 wherein the MDV used to infect the cell line is turkey herpesvirus strain FC126 and the immortal MDV infected cell line deposited as ATCC CRL-12052.

29. The method of claim 25 wherein the MDV used to infect the cell line is serotype 2 strain SB1 and the immortal MDV infected cell line deposited as ATCC CRL-12053.

30. The method of claim 25 wherein the MDV used to infect the cell line is serotype 1 MDV.

31. The method of claim 25 wherein the MDV is genetically engineered comprising one or more foreign genes inserted into one or more sites in the MDV.

32. The method of claim 25 wherein the immortal MDV infected cell line comprises a genetically engineered MDV having one or more MDV genes deleted.

33. An immortal MDV infected cell line wherein chick embryo cells are treated with a chemical mutagen to make an immortal cell line which is then infected with MDV to provide the MDV infected cell line that has phenotypic characteristics comprising: contact inhibited, anchorage dependent, non-tumorigenic, produces infectious MDV, invokes an immune response in avians, free of other avian viruses, and chicken helper factor (Chf) negative.

34. The immortal MDV infected cell line of claim 33 wherein the CEC cells are CHCC-OU2 cells deposited as ATCC CRL-12302.

35. The cell line of claim 33 wherein the MDV used to make the cell line is selected from the group consisting of serotype 1 MDV, serotype 2 MDV, or serotype 3 MDV, wherein serotype 3 MDV is turkey herpesvirus.

36. The cell line of claim 33 wherein the MDV used to infect the cell line is turkey herpesvirus strain FC126 and the immortal MDV infected cell line deposited as ATCC CRL-12052.

37. The cell line of claim 33 wherein the MDV used to infect the cell line is serotype 2 strain SB1 and the immortal MDV infected cell line deposited as ATCC CRL-12053.

38. The cell line of claim 33 wherein the MDV used to infect the cell line is serotype 1 MDV.

39. The cell line of claim 33 wherein the MDV is genetically engineered comprising one or more foreign genes inserted into one or more sites in the MDV.

40. The cell line of claim 33 wherein the immortal MDV infected cell line comprises a genetically engineered MDV having one or more MDV genes deleted.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
       ( A ) LENGTH: 22 Base Pairs
       ( B ) TYPE: Nucleic Acid
       ( C ) STRANDEDNESS: Single
       ( D ) TOPOLOGY: Linear ( i i ) MOLECULE TYPE:
       ( A ) DESCRIPTION: Synthetic DNA ( i i i ) HYPOTHETICAL: No ( i v ) ANTI-SENSE: No ( v i ) ORIGINAL SOURCE:
       ( A ) ORGANISM: Marek's Disease Virus ( v i i ) IMMEDIATE SOURCE:
       ( A ) LIBRARY:

( x i ) SEQUENCE DESCRIPTION: SEQ ID NO: 1:

TGCGATGAAA GTGCTATGGA GG                                                                            2 2

( 2 ) INFORMATION FOR SEQ ID NO:2:

( i ) SEQUENCE CHARACTERISTICS:
       ( A ) LENGTH: 22 Base Pairs
       ( B ) TYPE: Nucleic Acid
       ( C ) STRANDEDNESS: Single
       ( D ) TOPOLOGY: Linear ( i i ) MOLECULE TYPE:
       ( A ) DESCRIPTION: Synthetic DNA ( i i i ) HYPOTHETICAL: No ( i v ) ANTI-SENSE: No ( v i ) ORIGINAL SOURCE:
       ( A ) ORGANISM: Marek's Disease Virus ( v i i ) IMMEDIATE SOURCE:
       ( A ) LIBRARY:

( x i ) SEQUENCE DESCRIPTION: SEQ ID NO: 2:

GAGAATCCCT ATGAGAAAGC GC                                                                            2 2

( 2 ) INFORMATION FOR SEQ ID NO:3:

( i ) SEQUENCE CHARACTERISTICS:
       ( A ) LENGTH: 23 Base Pairs
       ( B ) TYPE: Nucleic Acid
       ( C ) STRANDEDNESS: Single
       ( D ) TOPOLOGY: Linear ( i i ) MOLECULE TYPE:
       ( A ) DESCRIPTION: Synthetic DNA ( i i i ) HYPOTHETICAL: No ( i v ) ANTI-SENSE: No ( v i ) ORIGINAL SOURCE:
       ( A ) ORGANISM: avian retrovirus ( v i i ) IMMEDIATE SOURCE:
       ( A ) LIBRARY: N/A ( x i ) SEQUENCE DESCRIPTION: SEQ ID NO: 3:

GCACCAAACA ATCTAGTCTG TGC                                                                                       23

( 2 ) INFORMATION FOR SEQ ID NO:4:

( i ) SEQUENCE CHARACTERISTICS:
        ( A ) LENGTH: 20 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: avian retrovirus     ( v i i ) IMMEDIATE SOURCE:
        ( A ) LIBRARY: N/A     ( x i ) SEQUENCE DESCRIPTION: SEQ ID NO: 4:

AAGTACTCAC TTCTCTGAAC                                                                                            20

( 2 ) INFORMATION FOR SEQ ID NO:5:

( i ) SEQUENCE CHARACTERISTICS:
        ( A ) LENGTH: 28 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: avian retrovirus     ( v i i ) IMMEDIATE SOURCE:
        ( A ) LIBRARY: N/A     ( x i ) SEQUENCE DESCRIPTION: SEQ ID NO: 5:

GCCAAGCTTC AATGAAGCAG AAGGCTTC                                                                                   28

( 2 ) INFORMATION FOR SEQ ID NO:6:

( i ) SEQUENCE CHARACTERISTICS:
        ( A ) LENGTH: 21 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: avian retrovirus     ( v i i ) IMMEDIATE SOURCE:
        ( A ) LIBRARY: N/A     ( x i ) SEQUENCE DESCRIPTION: SEQ ID NO: 6:

CAAATGAGGG TAATAAGGGA G                                                                                        21

( 2 ) INFORMATION FOR SEQ ID NO:7:

( i ) SEQUENCE CHARACTERISTICS:
        ( A ) LENGTH: 23 Base Pairs
        ( B ) TYPE: Nucleic Acid
        ( C ) STRANDEDNESS: Single
        ( D ) TOPOLOGY: Linear     ( i i ) MOLECULE TYPE:
        ( A ) DESCRIPTION: Synthetic DNA     ( i i i ) HYPOTHETICAL: No     ( i v ) ANTI-SENSE: No     ( v i ) ORIGINAL SOURCE:
        ( A ) ORGANISM: avian retrovirus     ( v i i ) IMMEDIATE SOURCE:
        ( A ) LIBRARY: N/A     ( x i ) SEQUENCE DESCRIPTION: SEQ ID NO: 7:

CACTACCAAA TATAATTCTG TAG                                                                                       23